(12) United States Patent
Shinkazh (10) Patent No.: US 7,988,859 B2
(45) Date of Patent: Aug. 2, 2011

(54) COUNTERCURRENT TANGENTIAL CHROMATOGRAPHY METHODS, SYSTEMS, AND APPARATUS

(75) Inventor: Oleg Shinkazh, Dedham, MA (US)

(73) Assignee: Chromatan Inc., Dedham, MA (US)

( * ) Notice: Subject to any disclaimer, the term of this patent is extended or adjusted under 35 U.S.C. 154(b) by 362 days.

(21) Appl. No.: 12/404,299

(22) Filed: Mar. 14, 2009

(65) Prior Publication Data

US 2010/0193434 A1 Aug. 5, 2010

Related U.S. Application Data

(60) Provisional application No. 61/150,240, filed on Feb. 5, 2009.

(51) Int. Cl.
*B01D 15/08* (2006.01)
(52) U.S. Cl. ........ 210/635; 210/650; 210/656; 210/659; 210/198.2
(58) Field of Classification Search .................. 210/635, 210/650, 651, 653, 654, 655, 656, 659, 198.2, 210/321.72, 321.75, 321.1, 321.84; 530/413, 530/414, 417
See application file for complete search history.

(56) References Cited

U.S. PATENT DOCUMENTS

| | | | | |
|---|---|---|---|---|
| 4,780,210 | A | 10/1988 | Hsia | |
| 6,383,380 | B1 * | 5/2002 | Kopf | 210/198.2 |
| 6,569,340 | B2 * | 5/2003 | Kopf | 210/635 |
| 6,596,172 | B1 * | 7/2003 | Kopf | 210/635 |
| 6,946,075 | B2 * | 9/2005 | Kopf | 210/635 |
| 2006/0118472 | A1 * | 6/2006 | Schick et al. | 210/198.2 |

* cited by examiner

*Primary Examiner* — Ernest G Therkorn
(74) *Attorney, Agent, or Firm* — American Patent Agency PC; Daniar Hussain; Cong Luo (57) ABSTRACT

This invention relates to a breakthrough in the art of chromatography allowing 1) larger scale of operation; 2) faster processing time; 3) disposability; 4) reduction of media/resin expenses; and 5) a reduction of capital equipment investment. In this invention, the chromatography column is replaced by a module that consists of two or more interconnected tangential flow filters and static mixers. The chromatography resin flows through this module in a single pass, while similar operations to a regular chromatographic process are performed on the resin (binding, washing, elution, regeneration, and equilibration). The buffers for these operations are pumped into the module in a countercurrent direction to the flow of resin, and permeate solutions from later stages are recycled back into previous stages. This creates concentration gradients in the permeate solutions of the tangential flow filters in the countercurrent direction to resin flow, thus saving buffer volume and increasing process efficiency.

10 Claims, 12 Drawing Sheets

COUNTERCURRENT TANGENTIAL CHROMATOGRAPHY METHODS, SYSTEMS, AND APPARATUS

REFERENCE TO RELATED APPLICATIONS

This applications claims priority from provisional application U.S. Ser. No. 61/150,240, filed on Feb. 5, 2009, and entitled "Counter Current Tangential Chromatography," the entirety of which is hereby incorporated by reference herein.

FIELD OF THE INVENTION

The present invention is generally related to chromatography. More specifically, this invention relates to a method, system, and apparatus of tangential chromatography using countercurrent flow to facilitate separation of the desired product and enhance efficiency of the entire chromatography process.

BACKGROUND OF THE INVENTION

There has been a significant and sustained growth in new drug production featuring monoclonal antibodies and other proteins, approximately 15-20% annually. This growth is due to expanding drug pipelines, as well as more efficient cell lines and bioreactor growth optimizations. The annual bioproduction costs are currently estimated at $2.6 billion. One of the most significant investments a drug manufacturer has to make is process chromatography (approximately 30% or $850 million annually).

Chromatography is an integral part of drug production; its purpose in the biotechnology industry is to purify the product proteins from contaminating species. The industry has started to recognize that the efficiency of the chromatography steps which are used to purify the product proteins are no longer keeping up with production demands. There are multiple reasons for this:

First, no significant improvements have been made to the column chromatography process in the past 30 years—most of the work in the industry has been focused on new resin development. A notable exception is membrane chromatography which was recently adopted by the industry.

Second, upstream technology has improved tremendously in the same time period—the bioreactors are larger (up to 20,000 liters), and the titers are much higher (up to 15 g/L compared with 1-2 g/L five years ago). As a result of longer fermentation times, there are generally more impurities in the bioreactor effluent solution. All of the above reasons result in a much heavier load for the downstream purification.

Third, column chromatography has inherent physical limitations. Columns larger than 2 meter in diameter do not scale up. The largest columns in the market are 2 meter diameter and 40 cm bed height. They fit 1,250 L of resin. Assuming a binding capacity of 30 g/L of resin (common Protein A resin capacity for monoclonal antibodies), a single cycle can bind 38 kg. A 20,000 L bioreactor with an output of 10 g/L would produce a load of 200 kg. This means that the biggest column in the market would have to run at least 6 full cycles to process a single batch. The operation can take up to 24 hrs and can result in a significant bottleneck for the manufacturing process.

Finally, in the present marketplace, disposability in the manufacturing process is gaining popularity. Disposable process steps save labor, do not require cleaning validation and are easier to run for the manufacturing personnel. Strides have been made in most downstream processes to have disposable systems. These are—bioreactors (up to 2,000 L volume Xcellerex Corp.), microfiltration (KleenPak TFF technology from Pall Corp.), depth filtration (POD, Millipore Corp.), sterile filtration (all major manufacturers), tangential flow filtration (all major manufacturers) and membrane chromatography (Mustang, Pall Corp., Sartobind, and Sartorius Corp.). The column chromatography technology because of its inherent limitation cannot be a part of the disposable trend. Therefore, it is currently impossible to have a completely disposable downstream process—a purification train must include a chromatography step which cannot be disposable.

Therefore, it was recognized by the present inventor that a breakthrough in the state of the art would include solutions to the above problems. It was recognized that the industry needs 1) larger scale of operation; 2) faster processing time; 3) disposability; 4) reduction of media/resin expenses; and 5) a reduction of capital equipment investment.

It is against this background that various embodiments of the present invention were developed.

BRIEF SUMMARY OF THE INVENTION

Therefore, one embodiment of the present invention is a scalable, reliable and disposable technology that utilizes a principle of recycling to significantly increase process efficiency, increase the scale of operation, and decrease resin costs.

In the present invention, the chromatography column is replaced by a module that consists of two or more interconnected tangential flow filters and static mixers. The chromatography resin flows through this module in a single pass, while similar operations to a regular chromatographic process are performed on the resin (binding, washing, elution, regeneration, and equilibration). The buffers for these operations are pumped into the module in a countercurrent direction to the flow of resin, and permeate solutions from later stages are recycled back into previous stages. This creates concentration gradients in the permeate solutions of the tangential flow filters in the countercurrent direction to resin flow, thus saving buffer volume and increasing process efficiency. The permeate solutions from binding, washing, equilibration and regeneration operations are put to waste. The permeate solution from the elution operation is the purified product stream which is collected in a separate product tank.

Accordingly, one embodiment of the present invention is a module 100 for countercurrent tangential chromatography (see FIG. 1) comprising a first input port (101) for receiving an input solution; a first mixer (102) for mixing the input solution with a recycled solution from a second input port (103) to produce a first mixer output; a stage I filter (104) for concentrating the first mixer output to produce stage I retentate, wherein stage I permeate solution exits the module from the stage I filter via a first output port (105); a second mixer (106) for mixing the stage I retentate from the stage I filter (104) and an optional buffer solution from a second input port (107); and a stage II filter (108) for concentrating an output from the second mixer (106) to produce stage II retentate which exits the module from the stage II filter via a second output port (110), wherein stage II permeate solution exits the module from the stage II filter via a third output port (109).

Another embodiment of the present invention is the module described above wherein the input solution comprises resin and unpurified product solution.

Another embodiment of the present invention is the module described above wherein the stage I permeate solution is waste.

Another embodiment of the present invention is the module described above wherein the stage I permeate solution is product.

Another embodiment of the present invention is the module described above wherein the second mixer receives clean buffer solution.

Another embodiment of the present invention is the module described above wherein the second mixer does not receive clean buffer solution.

Another embodiment of the present invention is the module described above wherein the third output port (109) is connected via a pump (112) and a three-way valve (111) to the second input port (103). (See FIG. 1.)

Another embodiment of the present invention is the module described above wherein the three-way valve (111) sends an output from the third output port (109) either to waste or product (113), or to the second input port (103). (See FIG. 1.)

Another embodiment of the present invention is the module described above wherein the stage I filter and the stage II filter are tangential flow filters.

Yet another embodiment of the present invention is a system (300) for countercurrent tangential chromatography (see FIG. 3) comprising a module (100) for countercurrent tangential chromatography; a first resin tank (302) for storing clean resin connected to a first input port (101) of the module; an input tank (304) for storing input solution connected to the first input port (101); a pump (112) and a three-way valve (111) interconnecting a second input port (103) with a third output port (109) of the module; a second resin tank (325) for storing resin connected to a second output port (110) of the module via a pump (323) and the three-way valve (317), and connected to the first input port (101) of the module via a pump (313); a product tank (309) for capturing product solution connected via a three-way valve (307) and a pump (308) to the first output port (105) of the module; and one or more buffer tanks (316, 318, 320, 322) for storing buffer solution connected to the third input port (107) of the module via a pump (314), wherein the first resin tank (302) is connected via 3-way valve (317) to second resin tank (325) and pump (323).

Another embodiment of the present invention is the system described above further comprising an additional countercurrent tangential chromatography stage comprising a third mixer (530) and a third filter (532), for increasing efficiency of the system. (See FIG. 5.)

Other embodiments of the present invention include the methods corresponding to the systems above, the systems constructed from the modules described above, and the methods of operation of the systems and modules described above. Other features and advantages of the various embodiments of the present invention will be apparent from the following more particular description of embodiments of the invention as illustrated in the accompanying drawings.

BRIEF DESCRIPTION OF THE DRAWINGS

FIG. 2A shows direction of flow in the module during binding mode, while

DETAILED DESCRIPTION OF THE INVENTION

Definitions: The following terms of art shall have the below ascribed meanings throughout this Specification.

Binding mode is a stage of operation during which resin and unpurified product form a reversible complex.

Washing mode is a stage of operation during which resin with bound product is washed with a washing buffer to rid the resin of impurities.

Elution mode is a stage of operation during which the complex of resin and the product is reversed and the purified product is collected.

Regeneration mode is a stage of operation during which the resin is cleaned for the purpose of reuse or for later cycles.

Equilibration mode is a stage of operation during which the system is equilibrated in a neutral buffer.

As stated in the Summary of the Invention section, in the present invention, the chromatography column is replaced by a module that consists of two or more interconnected tangential flow filters and static mixers. The chromatography resin flows through this module in a single pass, while similar operations to a regular chromatographic process are performed on the resin (binding, washing, elution, regeneration, and equilibration). The buffers for these operations are pumped into the module in a countercurrent direction to the flow of resin, and permeate solutions from later stages are recycled back into previous stages. This creates concentration gradients in the permeate solutions of the tangential flow filters in the countercurrent direction to resin flow, thus saving buffer volume and increasing process efficiency. The permeate solutions from binding, washing, equilibration and regeneration operations are put to waste. The permeate solution from the elution operation is the purified product stream which is collected in a separate product tank.

Figure 1:
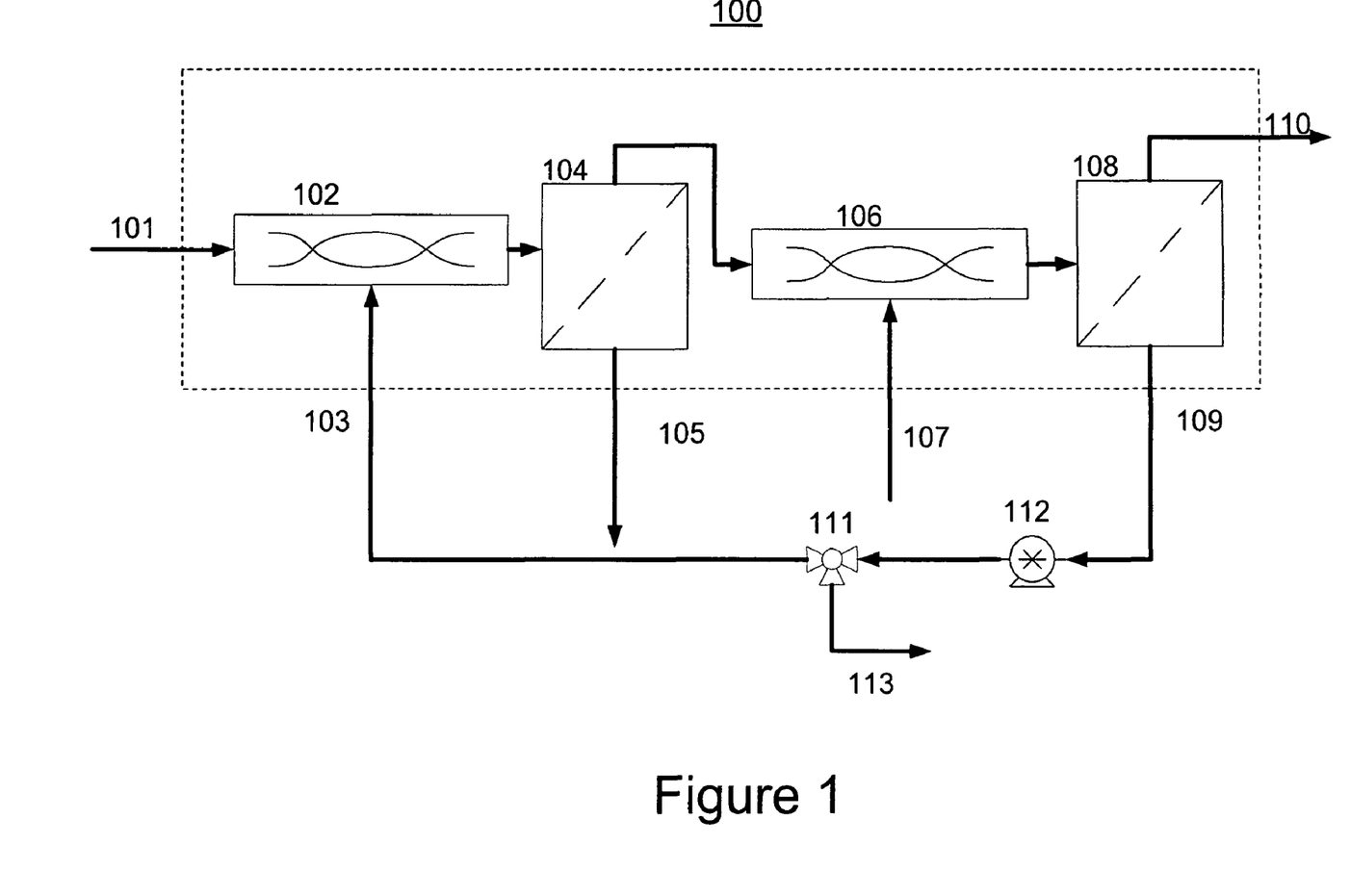
FIG. 1 shows a module for countercurrent tangential chromatography according to one embodiment of the present invention.

Accordingly, FIG. 1 shows a block diagram of a module 100 for countercurrent tangential chromatography (inside the dotted line). Input solution enters at port 101, and the input solution and any input from port 103 (none during binding mode) are mixed inside static mixer 102. The output from the static mixer 102 enters a tangential flow filter 104, from which the permeate exits the module at port 105. The retentate from tangential flow filter 104 is fed into static mixer 106, which may receive pure buffer at port 107. The output from static mixer 106 is fed into a tangential flow filter 108, from which permeate is pumped via pump 112 out of the module at port 109. Three-way valve 111 is utilized to direct flow either to waste 113 or to port 103. The retentate from tangential flow filter 108 exits the module at port 110. During washing, elution, equilibration and regeneration, three-way valve 111 directs the flow to port 103, where it mixes with input 101 in static mixer 102. During binding, three-way valve 111 directs the flow to waste 113.

Figure 2A:
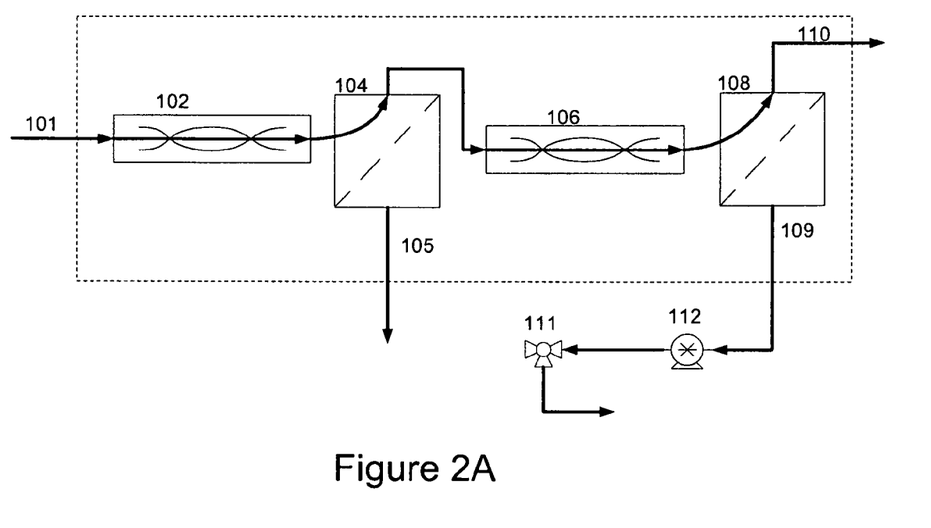

FIG. 2A shows direction of flow in module 100 of FIG. 1 during binding mode. Note the single-pass nature of the flow, and the fact that no flow enters at port 103 and port 107. The mixture of resin and non-purified product solution enter at the left through port 101 (through mixer 102), flows through filter 104 (with permeate exiting as waste at port 105), flows through mixer 106, flows through filter 108 (with permeate exiting as waste at port 109 via pump 112 and three-way valve 111), and exits the module at the right through port 110.

Figure 2B:
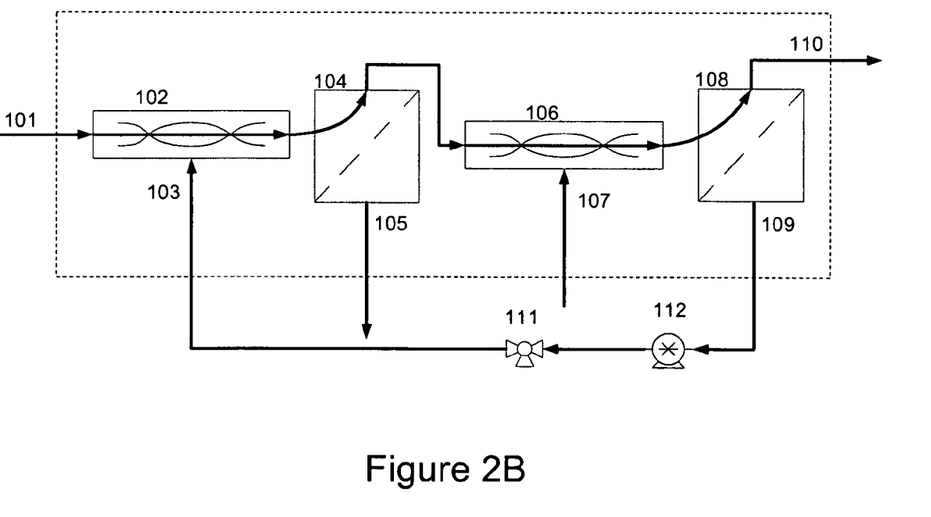
FIG. 2B shows direction of flow in the module during elution, washing, equilibration, and regeneration modes.

FIG. 2B shows direction of flow in module 100 during elution, washing, regeneration, and equilibration modes. Note the single-pass nature of the flow, and the fact that flow is recycled in a countercurrent direction from port 109 to port 103 via pump 112 and three-way valve 111. Note how in this configuration, clean buffer solution enters at port 107, and recycled buffer solution enters at port 103. Note also the countercurrent nature of the flow, where the solution being processed flows left-to-right as in FIG. 2A, while recycled buffer solution flows from right-to-left via pump 112 and three-way-valve 111, in a direction that is "counter-current" to the left-to-right flow of the solution being processed.

Figure 3:
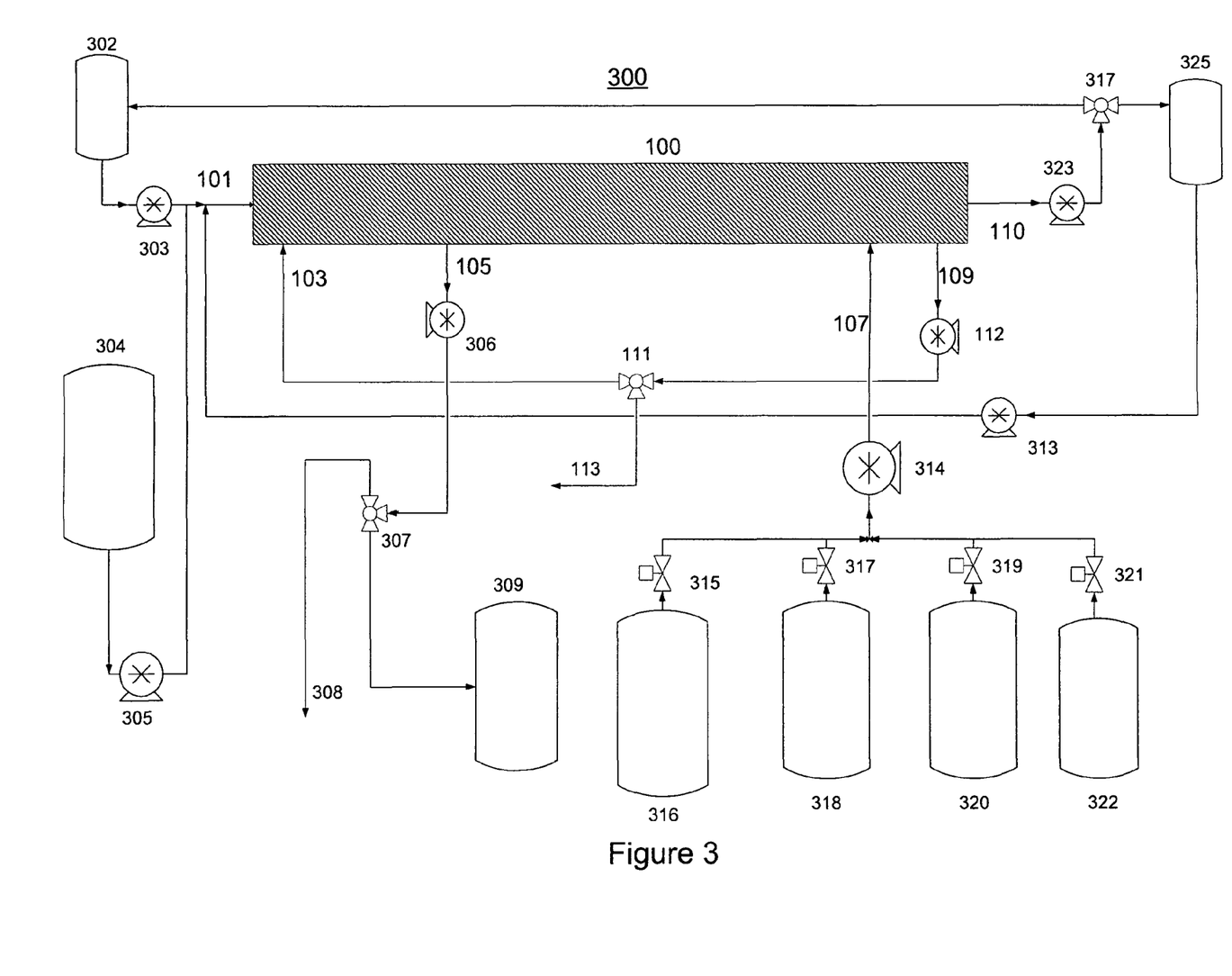
FIG. 3 shows a block diagram of a countercurrent tangential chromatography system operating in batch mode according to one embodiment of the present invention.

FIG. 3 shows a block diagram of a countercurrent tangential chromatography system 300 operating in batch mode according to another embodiment of the present invention. Module 100 operates in the same way as shown and described in relation to FIG. 1. Input port 101 of module 100 is connected to pumps 303, 305 and 313. Pump 303 pumps resin from first resin tank 302. Pump 313 pumps resin from second resin tank 325. Pump 305 pumps unpurified product solution from input tank 304. Port 103 of module 100 is connected via three-way valve 111 and pump 112 to port 109 of module 100, as shown in FIG. 1. Waste exits the system at 113. Output from port 105 is connected to pump 306, which is connected to a three-way valve 307. Three-way valve 307 is connected to product tank 309 and waste 308. Port 107 receives input into module 100 via pump 314, which is connected to equilibration tank 316, washing tank 318, elution tank 320 and regeneration tank 322 via valves 315, 317, 319 and 321. Output from port 110 is pumped via pump 323 and three-way valve 317 to the first resin tank 302 and a second resin tank 325.

The system in FIG. 3 is designed to treat the resin using a batch-mode operation. The resin is sequentially treated by different chromatographic processes (binding, washing, elution, regeneration, and equilibration) as it cycles from the first resin tank 302 to the second resin tank 325 and vice versa. For example, during the first stage (binding), resin passes from tank 302 to tank 325 from left to right through module 100 via pump 303. During the next stage (washing) resin passes from tank 325 to tank 302 from left to right through module 100 via pump 313. The other stages (elution, regeneration, and equilibration) alternate tanks in a similar manner. The countercurrent operation during washing, elution, regeneration, and equilibration allows greater efficiency and buffer conservation.

Figure 4:
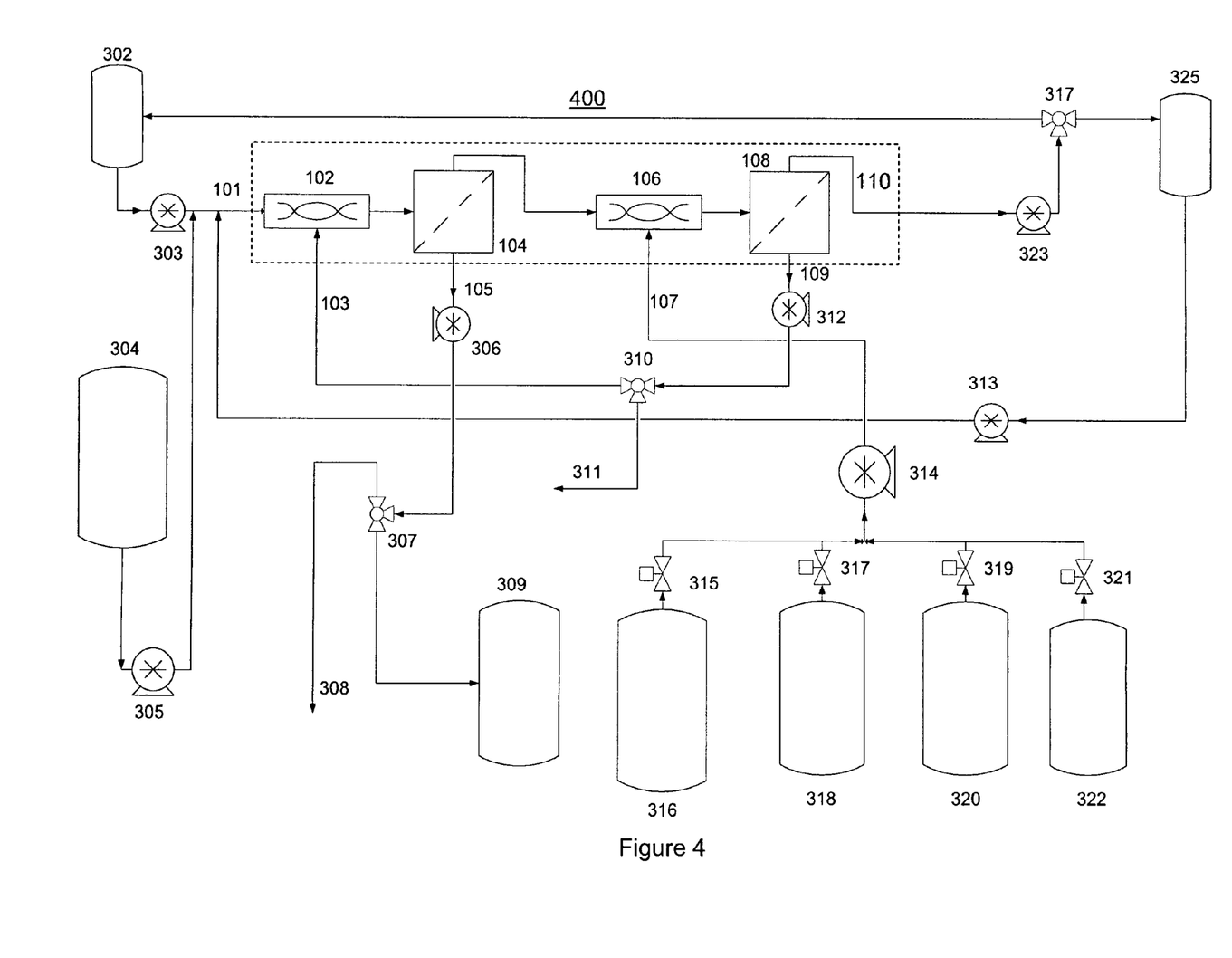
FIG. 4 shows another block diagram of the countercurrent tangential chromatography system of FIG. 3.

FIG. 4 shows a block diagram 400 of the countercurrent tangential chromatography system shown in FIG. 3, with the internal structure of module 100 shown. FIG. 4 is identical to FIG. 3 with the exception that the internals of module 100 are shown as in FIG. 1.

Figure 5:
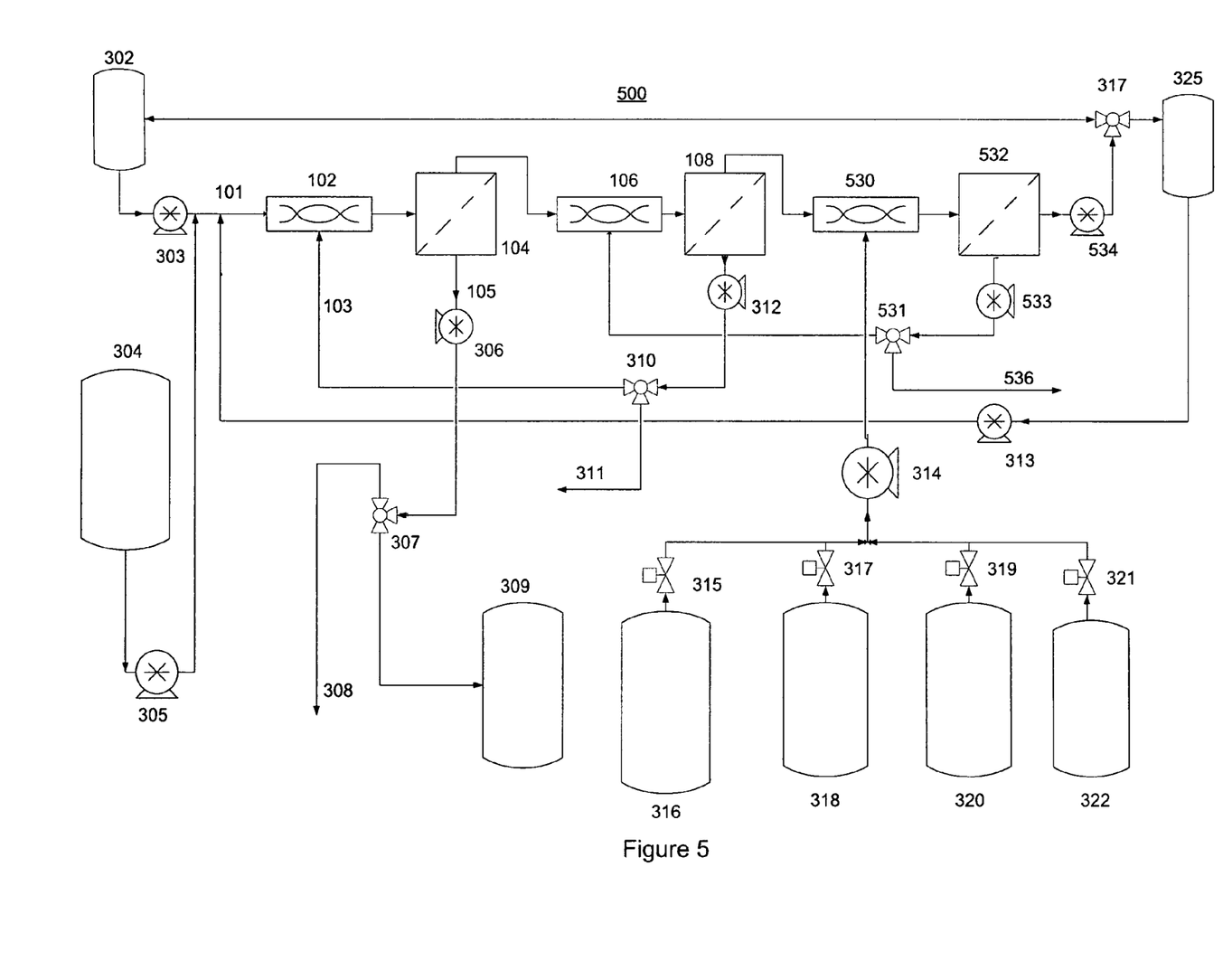
FIG. 5 shows a block diagram of another countercurrent tangential chromatography system according to another embodiment of the present invention.

FIG. 5 shows a block diagram 500 of another countercurrent tangential chromatography system 500 according another embodiment of the present invention. This embodiment is similar to FIGS. 3 and 4, except for addition of an additional (third) stage of countercurrent filtration, made up of mixer 530, filter 532, pump 533, and three-way valve 531, interconnected as shown in FIG. 5. Waste exits at 536. The embodiment shown in FIG. 5 operates in a manner analogous to the system shown in FIGS. 3 and 4, with the exception that flow passes through a third stage, which increases process efficiency and decreases buffer utilization, but introduces some complexity into the design. Mathematical modeling described below shows that using more than three stages produces no appreciable improvement in process efficiency while introducing substantial complexity. Hence, more than three stages, while possible according to the principles of the present invention and within the scope of the present invention, are not described further.

Figure 6:
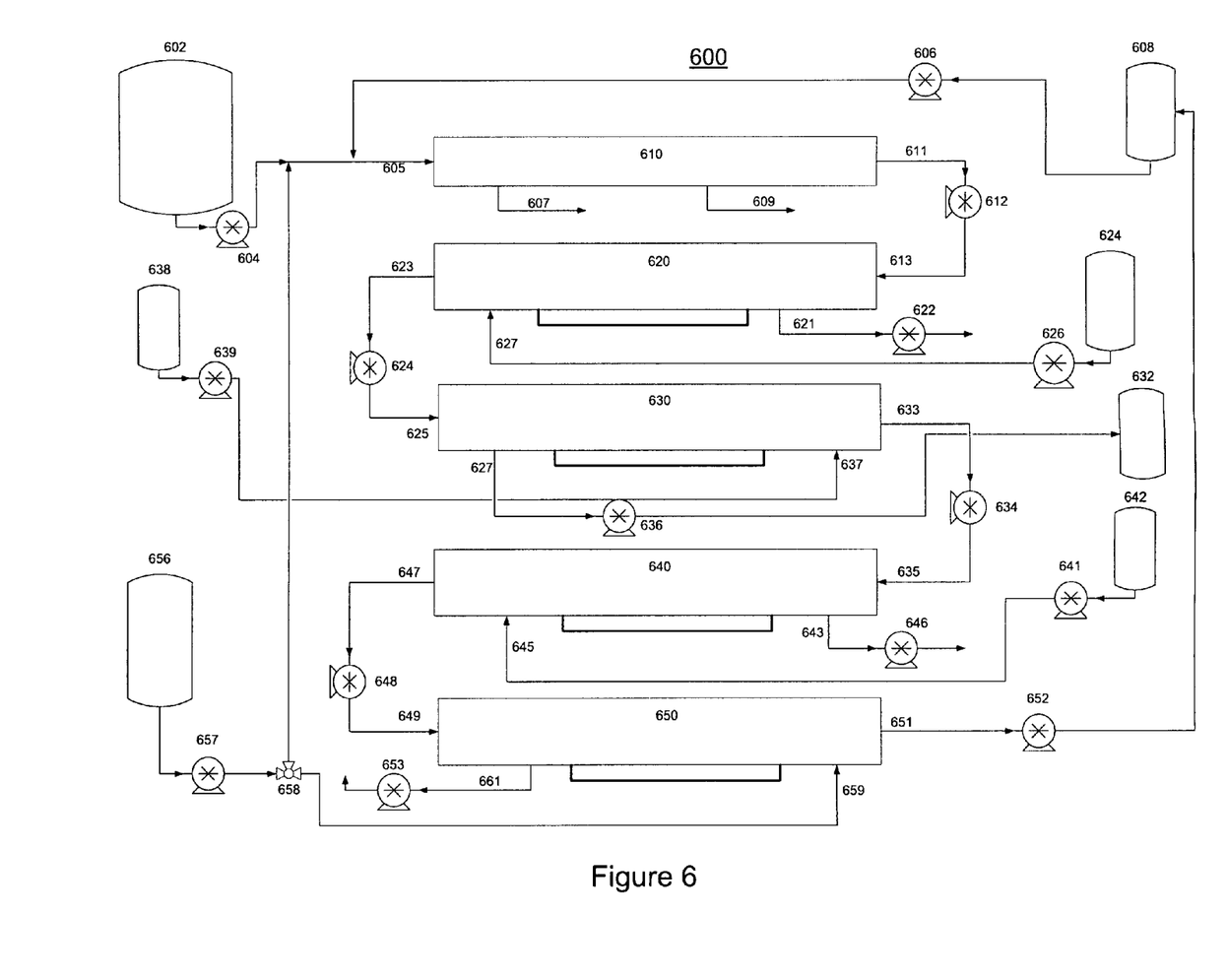
FIG. 6 shows a block diagram of another countercurrent tangential chromatography system operating in continuous mode, according to yet another embodiment of the present invention.

FIG. 6 shows a block diagram 600 of another countercurrent tangential chromatography system operating in continuous mode, according to yet another embodiment of the present invention. Modules 610 ("binding stage"), 620 ("washing stage"), 630 ("elution stage"), 640 ("regeneration stage") and 650 ("equilibration stage") operate in an analogous manner to the operation of module 100 shown in FIGS. 1, 2A and 2B. The thick black line on modules 620, 630, 640 and 650 represent a connection of a third output port (109) and a second input port (103) via pump (112) and three-way valve (111) on each module shown. These pumps and three-way valves are not shown in FIG. 6 for clarity, but they are present in each module 620, 630, 640 and 650 as shown in FIG. 1. Note that module 610 ("binding stage") does not have its third output port (609) nor its second input port (607) interconnected, since in this module both port 609 and port 607 go to waste.

Binding stage module 610 is connected at port 605 via pump 604 to non-purified product tank 602, via pump 606 to resin tank 608, and via three-way valve 658 and pump 657 to equilibration buffer tank 656. Ports 607 and 609 on module 610 go to waste.

Washing stage module 620 is connected at port 613 via pump 612 to an output port 611 of the binding stage module 610. Port 621 goes to waste via pump 622. Washing buffer enters at port 627 via pump 626 from washing buffer tank 624.

Elution stage module 630 is connected at port 625 via pump 624 to output port 623 of washing stage module 620. Elution buffer enters at port 637 via pump 639 from elution buffer tank 638. Purified product exits module 630 at port 627 via pump 636 into product storage tank 632.

Regeneration module 640 is connected at port 635 via pump 634 to output port 633 of module 630. Waste exits at port 643 via pump 646. Regeneration buffer enters at port 645 via pump 641 from regeneration buffer tank 642.

Equilibration module 650 is connected at port 649 via pump 648 to output port 647 of regeneration module 640. Resin is pumped out of port 651 via pump 652 into the resin storage tank 608. Waste is pumped from module 650 at port 661 via pump 653. Equilibration buffer enters at port 659 via the three-way valve 658 and the pump 657 from the equilibration buffer tank 656.

Accordingly, unlike the system of FIG. 3, which is designed to treat the resin/product in alternating batch-mode, with resin alternating between the first and the second resin tanks, the system of FIG. 6 is designed to treat the resin/product in a single continuous pass, with resin flowing continuously from the resin tank 608, through modules 610, 620, 630, 640, and 650, and returning to resin tank 608. The continuous nature of the system shown in FIG. 6 allows a fixed amount of resin to be used for processing an essentially unlimited amount of unpurified product, subject only to the lifetime of the resin.

Figure 7A:
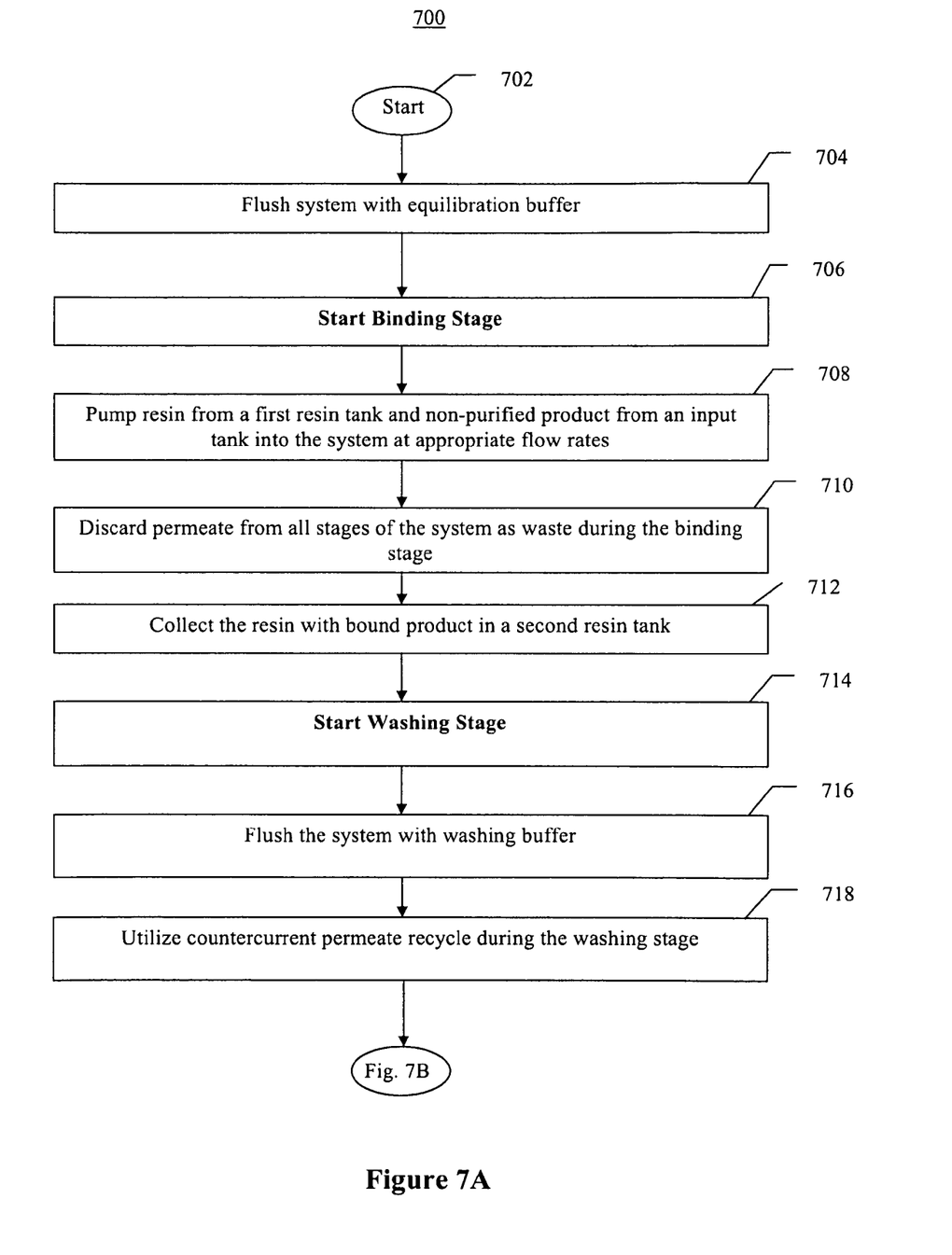
FIGS. 7A, 7B, and 7C show a flowchart of a process of countercurrent tangential chromatography operating in batch mode, according to yet another embodiment of the present invention.
Figure 7B:
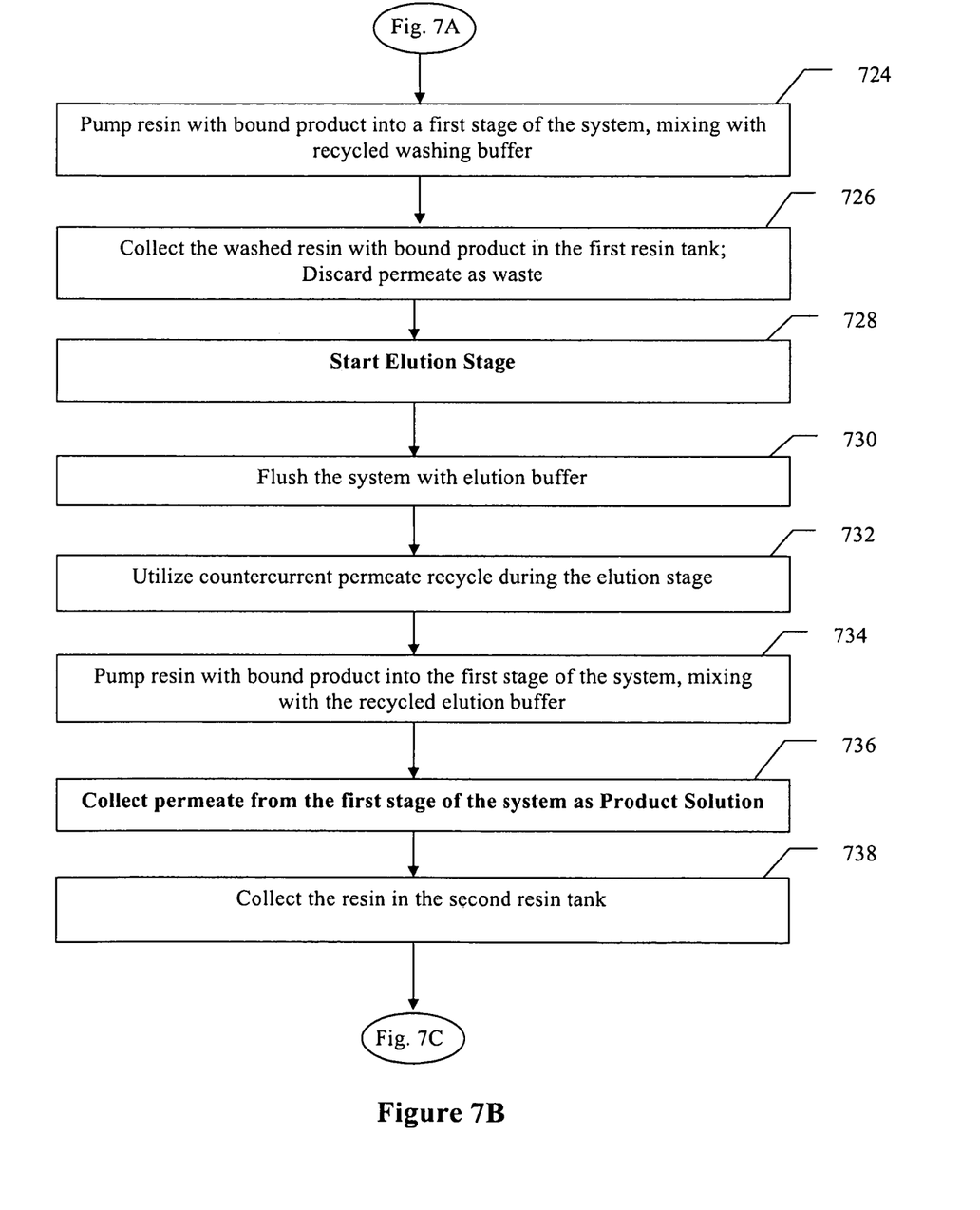
Figure 7C:
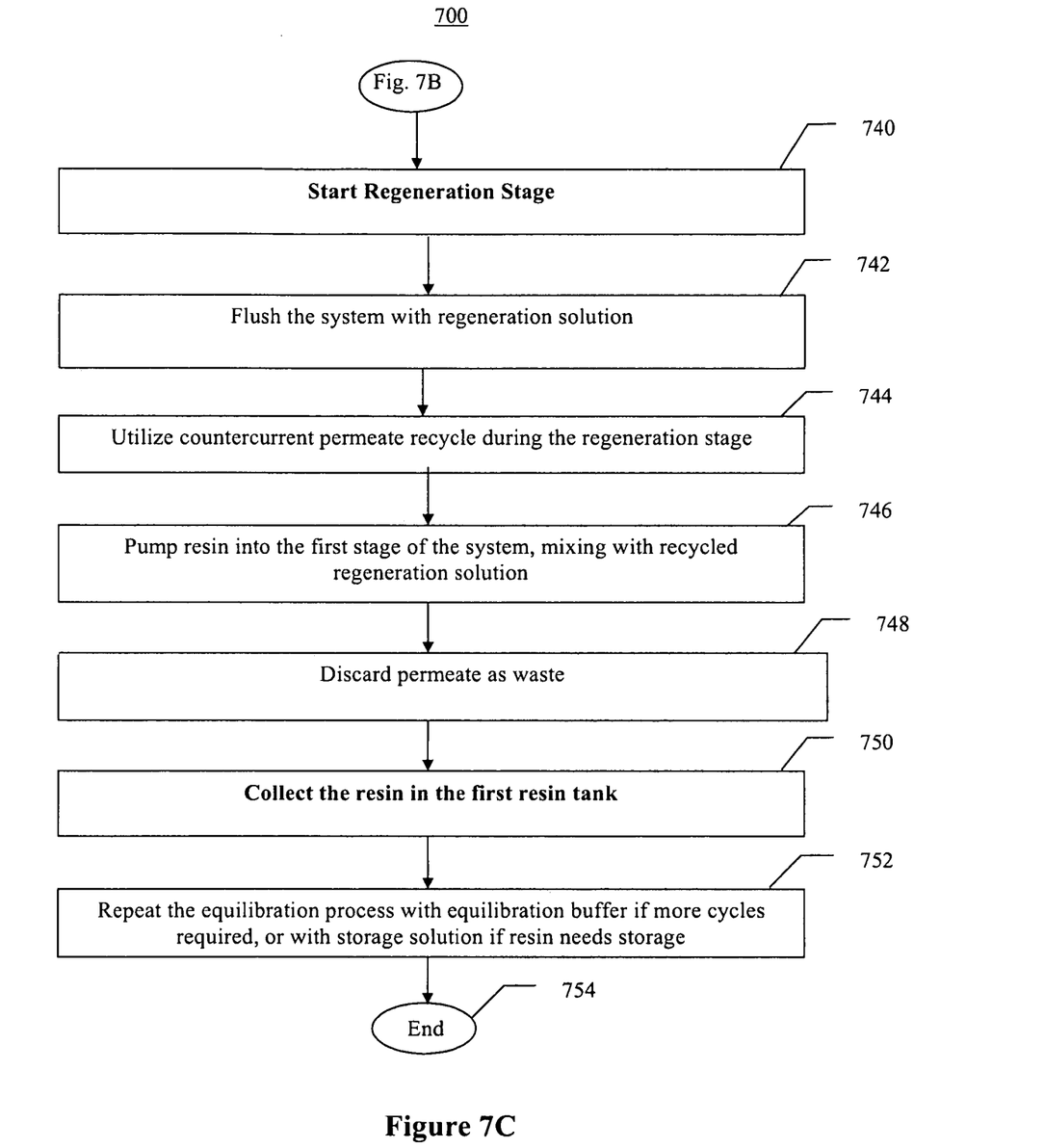

FIGS. 7A, 7B, and 7C show a flowchart of a process 700 of countercurrent tangential chromatography operating in batch mode, according to yet another embodiment of the present invention. Process 700 begins at step 702. The system is flushed with equilibration buffer, as shown in step 704. In step 706, the binding stage is started (emphasis in bold). Resin and non-purified product is pumped into the system at appropriate flow rates, as shown in step 708. The permeate solutions are discarded from all stages as waste during the binding stage only, as shown in step 710. The resin is collected with bound product as shown in step 712.

In step 714, the washing stage is started (emphasis in bold). The system is flushed with washing buffer, as shown in step 716. The countercurrent permeate is recycled and utilized during the washing stage to improve process efficiency and conserve buffer solution according to the principles of the present invention, as shown in step 718. Resin is pumped with bound product back into the first stage of the system, where it mixes with the recycled wash buffer, as shown in step 724. The washed resin with bound product is collected in the first resin tank, while permeate solution is discarded as waste, as shown in step 726.

In step 728, the elusion stage is started (emphasis in bold). The system is flushed with elution buffer, as shown in step 730. The countercurrent permeate is recycled and reused during the elution stage in order to improve process efficiency and to conserve buffer solution, as shown in step 732. Resin bound with product is pumped back into the first stage of the system, where it mixes with the recycled elusion solution, as shown in step 734.

In step 736, permeate solution from the first stage is collected as product solution (emphasis in bold). Resin is collected in the second resin tank, as shown in step 738.

In step 740, the regeneration stage is started (emphasis in bold). The system is flushed with regeneration solution, as shown in step 742. The countercurrent permeate is recycled and reused during the regeneration stage, in order to improve process efficiency and to conserve buffer solution, as shown in step 744. The resin is pumped into the first stage, where it mixes with the recycled regeneration solution, as shown in step 746. The permeate solution is discarded as waste, as shown in step 748.

In step 750, the resin is collected in the first resin tank (emphasis in bold), hence completing the cycle and allowing the reuse of resin.

Finally, the equilibration process using equilibration buffer may be repeated if more cycles are required, as shown in step 752. Alternatively, equilibration process may be performed with storage solution if the resin requires storage, as shown in step 752. The process 700 ends in step 754.

Figure 8:
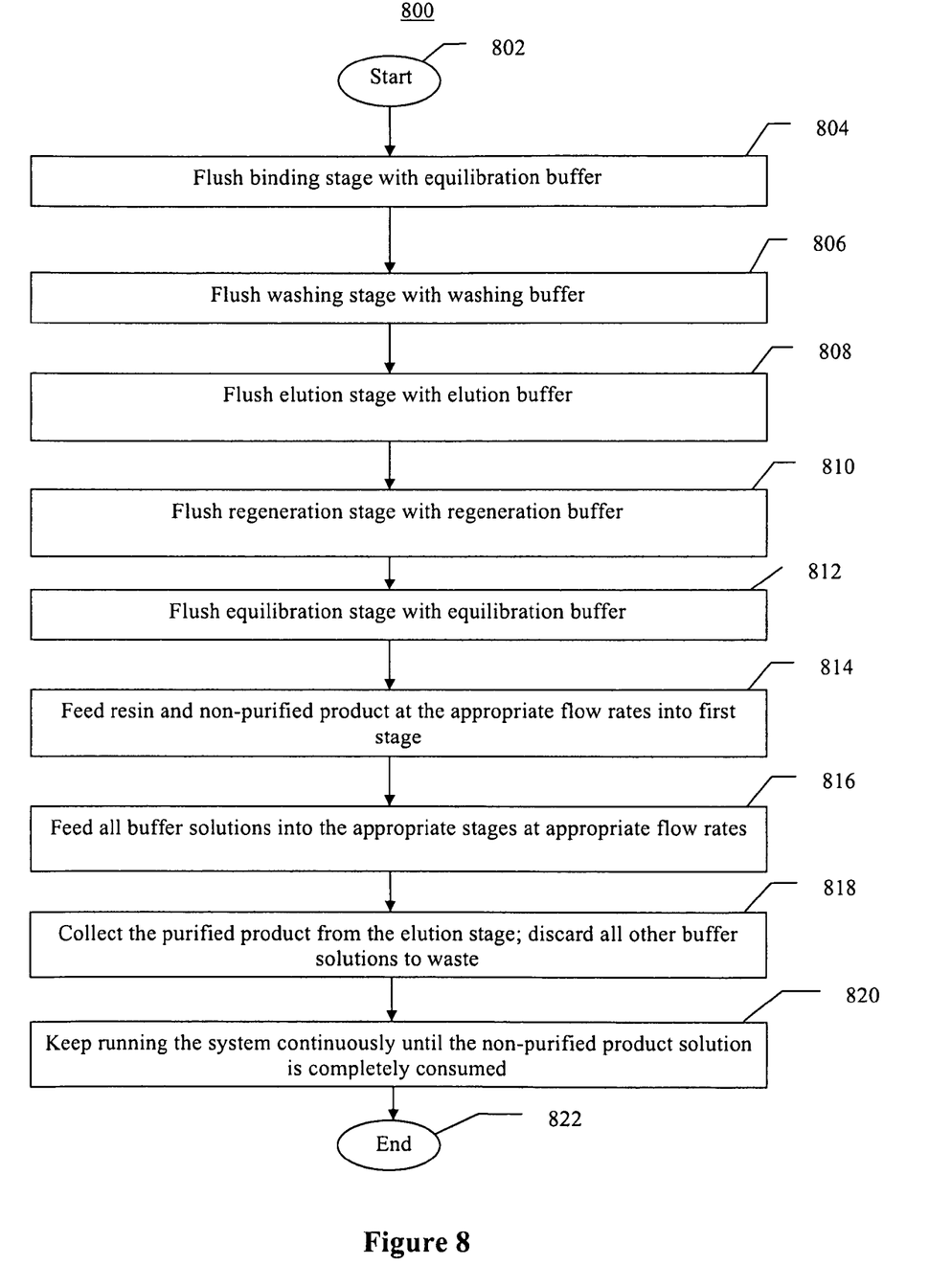
FIG. 8 shows a flowchart of a process of countercurrent tangential chromatography operating in continuous mode, according to yet another embodiment of the present invention.

FIG. 8 shows a flowchart of a process 800 of countercurrent tangential chromatography operating in continuous mode, according to yet another embodiment of the present invention. Process 800 begins in step 802. The binding stage (Module 610 of FIG. 6) is flushed with equilibration buffer, as shown in step 804. The washing stage (Module 620 of FIG. 6) is flushed with washing buffer, as shown in step 806. The elution stage (Module 630 of FIG. 6) is flushed with elution buffer, as shown in step 808. The regeneration stage (Module 640 of FIG. 6) is flushed with regeneration buffer, as shown in step 810. The equilibration stage (Module 650 of FIG. 6) is flushed with equilibration buffer, as shown in step 812. Resin and non-purified product are fed at the appropriate flow rates into the first stage of the system (Module 610 of FIG. 6), as shown in step 814. All buffer solutions are fed into the appropriate stages at appropriate flow rates, as shown in step 816. The purified product is collected from the elution stage (Module 630 of FIG. 6), while all other buffer solutions are discarded to waste, as shown in step 818. The entire system is kept running continuously until the non-purified product solution is completely consumed, as shown in step 820. The process 800 ends in step 822.

Modeling

Product recovery is one of the most important cost drivers in chromatography. This is because the protein molecules are of extremely high value. A capture chromatography process should have a recovery of at least 90%. Therefore, it was decided to model the product recovery stage of the present invention (the elution stage).

The following assumptions were made in this model:

1. The tangential flow (TFF) membranes in the module are able to process the slurry of resin and elution buffer at appropriate conversion factors (upwards of 80%).
2. The kinetics of desorption of the product molecule from the resin is fast.
3. The sieving coefficient of the TFF membrane is constant through ought the process.
4. The system is "dead-space" free.

The impact on the percent yield (% recovery) of the following variables are explored in this model:

1. "Gamma ($\gamma$)" is the ratio of elution buffer flow-rate to resin buffer flow rate, and governs the dilution of the product, buffer usage, and washing efficiency. This variable can be controlled by the operator.
2. "s" is the sieving coefficient of the TFF membrane for the product molecule. s equals the product concentration in the permeate divided by the product concentration in the retentate. This is an inherent property of the membrane and cannot be changed by the operator.
3. "N" is the number of stages; the present model explores a two-stage and a three-stage system in operation. As the number of stages increases, the washing efficiency and product recovery increases, with all other variables are held constant. However, more stages increase the complexity and cost of the system.

Model equations were derived by using material balances and solving for % yield. It became convenient to introduce a new variable $\alpha = \gamma \cdot s$.

Equation 1 shows the percent-yield for a two-stage system as a function of $\alpha$:

$$\% \text{ Yield} = \left(1 - \frac{1}{(1 + \alpha + \alpha^2)}\right) * 100\% \quad (1)$$

Equation 2 shows the percent-yield for a three-stage system as a function of $\alpha$:

$$\% \text{ Yield} = \left(1 - \frac{1}{(1 + \alpha + \alpha^2 + \alpha^3)}\right) * 100\% \quad (2)$$

Figure 9:
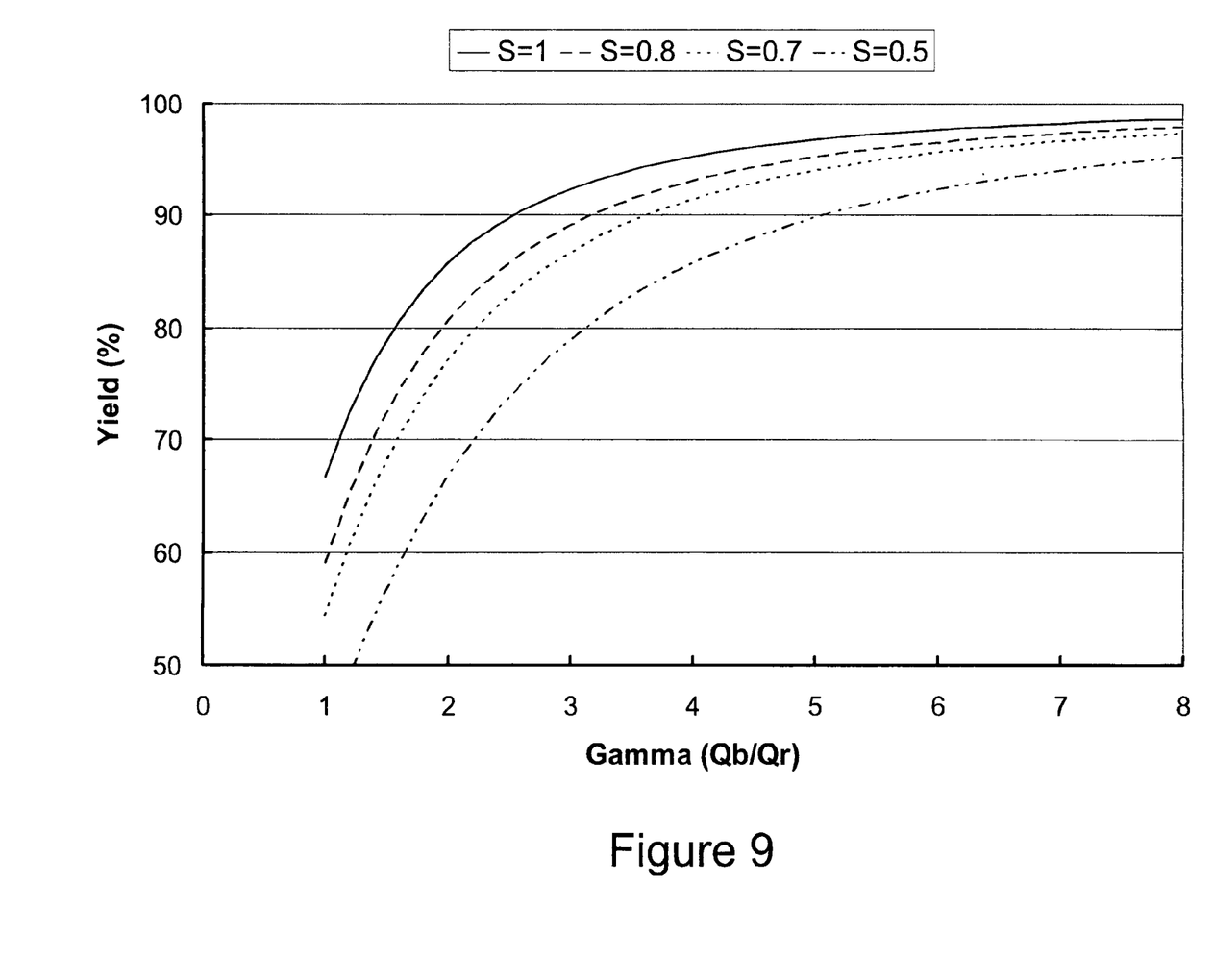
FIG. 9 shows results of a mathematical model of a two-stage countercurrent tangential chromatography system according to the principles of the present invention, showing a ratio of buffer to resin flow-rates (gamma) vs. percent yield for various sieving coefficients.
Figure 10:
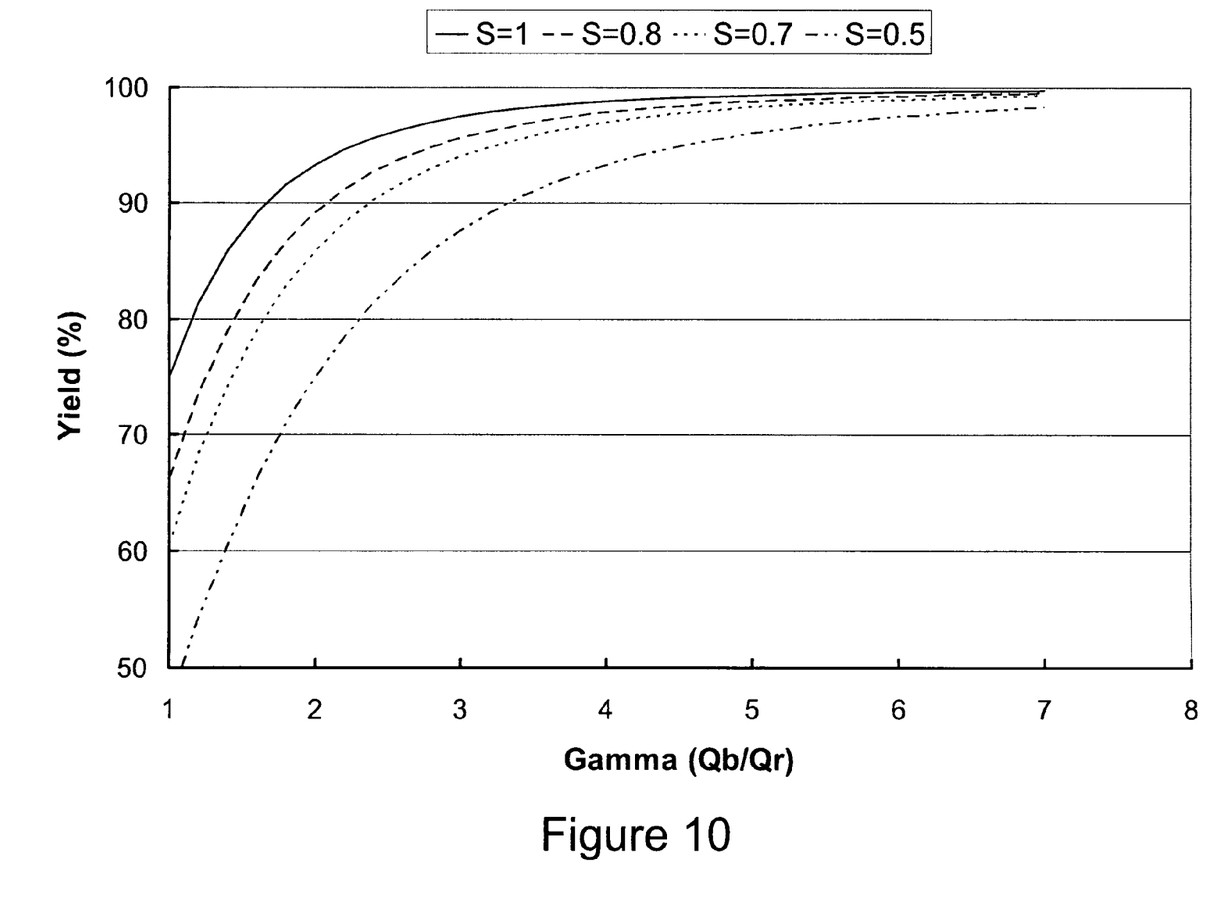
FIG. 10 shows results of a mathematical model of a three-stage countercurrent tangential chromatography system according to the principles of the present invention, showing a ratio of buffer to resin flow-rates (gamma) vs. percent yield for various sieving coefficients.

FIGS. 9 and 10 show the results of this model; gamma ($\gamma$) is the independent variable, and percent (%) yield is the dependent variable. Percent yield curves are generated for specific sieving coefficients for both models (s=0.5, 0.7, 0.8, 1.0).

FIG. 9 shows the results for a two-stage countercurrent tangential chromatography system showing the ratio of buffer to resin flow-rates (gamma) vs. percent yield for sieving coefficients s=0.5, 0.7, 0.8, 1.0.

FIG. 10 shows the results for a three-stage countercurrent tangential chromatography system showing the ratio of buffer to resin flow-rates (gamma) vs. percent yield for sieving coefficients s=0.5, 0.7, 0.8, 1.0.

The results of the model show that greater than 95% yield can be achieved by both the two-stage and the three-stage systems. Sieving coefficients for these processes are expected to be within a range of [0.8-1.0] because the membranes used in this system would be microporous and would therefore be expected to pass the product molecule relatively freely. The two-stage system would need a higher buffer to feed ratio ($\gamma$) than the three-stage system to achieve the same percent (%) yield. Therefore, the recommended operating gamma ($\gamma$) for a two-stage system is 4 to 6, and for a three-stage system the recommended operating gamma ($\gamma$) is 3 to 4.

A modeling example is described here of protein A capture of 20,000 L bioreactor harvest, 5 g/L IgG concentration, in a three-stage countercurrent tangential chromatography system operating in batch mode, as shown in FIG. 5. This example is illustrative of one of many modes of operation of the present invention.

This modeling example makes the following assumptions:
1. Residence time=0.5 min (hypothetical "small" protein A bead)
2. Resin capacity=30 g/L
3. General Electric® hollow fibers are used as the TFF membrane. The areas and hold up volumes are used from existing large scale General Electric® modules.
4. Flux=100 LMH
5. An 80% conversion factor is assumed in the TFF filters.

TABLE 1

Modeling results

| | |
|---|---|
| Volume | 20000 L |
| Product conc. | 5 g/L |
| Total product | 100 kg |
| Total Membrane area | 300 m2 |
| # of stages | 3 |
| Washing dilution factor | 4 |
| Resin Volume | 300 L |
| Resin Capacity | 30 g/L |
| Flux | 100 LMH |
| One cycle processes | 9 kg MAB |
| One cycle Volume | 1800 L |
| Residence time | 0.5 min |
| Static mixer volume | 100 L |
| Total Flow | 200 L/min |
| Resin Flow rate | 28.6 L/min |
| Feed Flow rate | 171.4 L/min |
| Feed Flux | 34.3 LMH |
| Binding stage time | 0.175 hrs |
| Wash Volume 4 Resin Volumes (RV) | 1200 L |
| Washin stage Time | 0.120 hrs |
| Elution Volume 4 Resin Volumes (RV) | 1200 L |
| Elution stage Time | 0.12 hrs |
| Regeneration Buffer volume (4 RV) optional | 1200 L |
| Wash Time | 0.120 hrs |
| Equilibration Buffer volume (4 RV) | 1200 |
| Wash Time | 0.120 hrs |
| Total Cycle time | 0.66 hrs |
| # of cycles | 12 |
| Total Processing Time | 7.9 hrs |

The results of this model show the following:
1. 20,000 L of unpurified product can be processed with 300 L of resin which represents a factor of 4 decrease from conventional column chromatography.
2. The operation can be performed in a single 8-hr shift.
3. Number of cycles can be decreased by increasing resin volume.
4. Efficiency and process time could be increased by increasing flux.

The inventor recognizes numerous and substantial advantages of the present invention to the downstream purification process, including:

1. Current technology could be readily adapted to this process because existing components are readily available in the market. Namely, the tangential flow filters (cassettes, hollow fibers and ceramic membranes) and chromatography resins are readily available. It might be advantageous to develop a new line of resins specifically designed for this invention by using smaller beads than in conventional column chromatography. This would nullify mass transfer limitations, increase dynamic binding capacity, and make the process more efficient.

2. Tangential chromatography systems according to the principles of this invention may be scaled as large as necessary, similarly to any tangential flow system. This is not the case with conventional column chromatography—the largest scalable columns in the market are currently limited to 2 meters in diameter.

3. Continuous-mode countercurrent tangential chromatography can be designed as shown in FIG. 6. In general, continuous processes are more efficient and require a smaller system size.

4. There is potential to run this system in a completely disposable manner. This is because much smaller amounts of resin are needed for this operation than in column chromatography (this would be true for cheaper resin kinds such as ion exchange resins). Additionally, the tangential flow filters at smaller scales could be used on a disposable basis as well.

5. The use of resin could be an order of magnitude lower than in conventional chromatography, causing significant cost savings by as much as 80%.

Therefore, the present inventor recognizes numerous applications of the present invention to the $850+ million/year process chromatography market.

U.S. Pat. No. 4,780,210 to Jen-Chang Hsia entitled "Tangential flow affinity ultra-filtration" describes a process for trypsin purification. More particularly, it relates to a process of biochemical purification which combines the processing techniques of affinity chromatography and tangential ultra-filtration, and is capable of being operated on a continuous flow or semi-continuous-flow basis, for use in the purification (or separation) of molecules of biological interest. The process of the present invention is verifiably different because of the countercurrent and single-pass nature, along with various other improvements. The process described in U.S. Pat. No. 4,780,210 is not suitable for the biotech market.

Accordingly, while the methods disclosed herein have been described and shown with reference to particular operations performed in a particular order, it will be understood that these operations may be combined, sub-divided, or re-ordered to form equivalent methods without departing from the teachings of the present invention. Accordingly, unless specifically indicated herein, the order and grouping of the operations is not a limitation of the present invention.

Finally, while the invention has been particularly shown and described with reference to particular embodiments thereof, it will be understood by those skilled in the art that various other changes in the form and details may be made without departing from the spirit and scope of the invention, as defined in the appended claims.

What is claimed is:

1. A module, comprising:
a first input port for receiving an input solution;
a first mixer for mixing the input solution with a recycled solution from a second input port to produce a first mixed output;
a stage I filter for concentrating the first mixed output to produce stage I retentate, wherein stage I permeate exits the module from the stage I filter via a first output port;
a second mixer for mixing the stage I retentate from the stage I filter and an optional buffer solution from a third input port to produce a second mixed output; and
a stage II filter in series with the stage I filter for concentrating the second mixed output to produce stage II retentate which exits the module from the stage II filter via a second output port, wherein stage II permeate exits the module from the stage II filter via a third output port, wherein the input solution from input port flows through the stage I filter and the stage II filter in a single pass, and recycled solution from the third output port flows countercurrent to the input solution into the second input port.

2. The module of claim 1, wherein the input solution comprises resin slurry and unpurified product solution.

3. The module of claim 1, wherein the stage I permeate is waste.

4. The module of claim 1, wherein the stage I permeate is product.

5. The module of claim 1, wherein the second mixer receives clean buffer solution.

6. The module of claim 1, wherein the second mixer does not receive clean buffer solution.

7. The module of claim 1, wherein the third output port is connected via a pump and a three-way valve to the second input port.

8. The module of claim 7, wherein the three-way valve sends an output from the third output port either to waste, or to the second input port.

9. The module of claim 1, wherein the stage I filter and the stage II filter are tangential flow filters.

10. The module of claim 1, wherein the first mixer and the second mixer are static mixers.

* * * * *